United States Patent [19]

Foster

[11] Patent Number: 4,676,950

[45] Date of Patent: Jun. 30, 1987

[54] INDICATOR AND TEST DEVICE FOR DETECTING OCCULT BLOOD

[75] Inventor: Raymond O. Foster, Joliet, Ill.

[73] Assignee: Foster Research Corporation, Joliet, Ill.

[21] Appl. No.: 576,811

[22] Filed: Feb. 3, 1984

[51] Int. Cl.$^4$ ............... G01N 21/78; G01N 33/52; G01N 33/72

[52] U.S. Cl. ............... 422/56; 422/57; 436/66

[58] Field of Search ............... 436/66, 169; 422/56, 422/57

[56] References Cited

U.S. PATENT DOCUMENTS

| | | |
|---|---|---|
| 2,290,436 | 7/1942 | Kamlet . |
| 2,799,660 | 7/1957 | Nichoils et al. . |
| 2,838,377 | 6/1958 | Fonnor . |
| 3,012,976 | 12/1961 | Adams, Jr. et al. . |
| 3,092,463 | 6/1963 | Adams, Jr. et al. . |
| 3,092,464 | 6/1963 | Adams, Jr. et al. . |
| 3,252,762 | 5/1966 | Adams, Jr. et al. . |
| 3,290,117 | 12/1966 | Adams, Jr. et al. . |
| 3,853,472 | 12/1974 | Rittersdorf et al. ............... 436/66 |
| 4,063,894 | 12/1977 | Ogawa et al. ............... 436/66 |
| 4,129,417 | 12/1978 | White ............... 436/66 X |
| 4,148,611 | 4/1979 | Nand et al. ............... 436/66 |
| 4,157,894 | 6/1979 | Bombardelli ............... 436/94 |
| 4,219,336 | 8/1980 | Guthlein et al. ............... 436/66 |
| 4,278,763 | 7/1981 | Berger et al. ............... 436/87 X |

*Primary Examiner*—Barry S. Richman
*Assistant Examiner*—Robert J. Hill, Jr.
*Attorney, Agent, or Firm*—Leydig, Voit & Mayer

[57] ABSTRACT

A test composition for detecting occult blood includes an alkaline water insoluble fraction of guaiac, an organic hydroperoxide containing a tertiary hydroperoxide group, and a buffer capable of maintaining the pH of material being tested within the range of about 4.5 to about 6.8, the purified guaiac, the hydroperoxide and the buffer being present in an amount effective to produce a color change in the presence of a hemoglobin-containing material. The test composition may be combined with a test substrate, preferably a matrix of bibulous or cellulosic material to provide a test device for detecting occult blood.

14 Claims, No Drawings

INDICATOR AND TEST DEVICE FOR DETECTING OCCULT BLOOD

TECHNICAL FIELD

The present invention relates to an improved diagnostic composition and a test device employing the composition. More particularly, this invention relates to a test composition and device useful for the detection of occult blood found in bodily fluids and products of elimination such as urine, vomitus, gastro-intestinal contents, cerebrospinal fluids and particularly feces. The present invention is concerned, in particular, with a highly sensitive reagent composition for the detection of occult blood, which composition may be incorporated into a bibulous carrier, thereby forming an accurate and sensitive test device for occult blood.

BACKGROUND ART

The detection of occult blood in body fluids and body excreta provides valuable assistance to physicians in the diagnosis of a number of abnormal physical conditions. Blood may be found in the gastric contents and in vomitus in conditions which are associated with erosion of gastric and intestinal mucous membranes, in ulcers and in carcinomas. The regular and frequent occurrence of occult blood in feces is suggestive of colon-rectal cancer, gastric or duodenal ulcers or hemorrhoids. In many of these conditions, the hemorrhage may be so slight that it is not possible to detect blood by microscopic identification, even by a skilled technician.

What has long been sought is a simple diagnostic test, rapidly and easily performed, which can be unequivocally interpreted by one with limited technical skills. Numerous tests and test devices have been and are available to the medical practitioner for detecting occult blood. However, almost all of these tests suffer from one or more shortcomings, such as an overly complex procedure, too lengthy a procedure or time required for obtaining results, or difficulties in interpreting results due to the level of skill required, false positives, or generally equivocal results.

A commonly employed test currently used to detect occult blood employs a test device in which a paper strip impregnated with a water soluble indicator system is dabbed with a sample of the specimen being tested. A positive test is indicated by a color change in the indicator test strip. Although such a device and method permit rapid performance of the test, results are sometimes difficult to interpret. This is attributable at least in part to the nature of the materials employed in the test strip and sample. That is, the use of a water soluble indicator composition in a paper test strip for detecting blood in an aqueous-based medium renders interpretation of test results difficult since the water soluble color indicator composition tends to migrate or diffuse through the paper matrix.

Similar test devices employ paper test strips impregnated with color indicator compositions which are at least in part water insoluble, thereby avoiding diffusion of the "test spot". However, these strips require the user to have and to apply a separate reagent at the time the test is performed in order to develop the color.

DISCLOSURE OF INVENTION

The present invention relates to an indicator composition for detecting occult blood and to a test device incorporating same, which composition and test device provide relatively inexpensive, simply performed and easily interpreted diagnostic tests. The test, employing the color indicator composition or test device of the present invention, may be performed with equal ease by persons with little or no training in laboratory technique as well as by the skilled laboratory technician or physician.

The present invention provides a test device in which all necessary test reagents are incorporated therein. Thus, it is not necessary to have nor to apply additional reagents to the test device in order to satisfactorily perform the diagnostic test.

The present invention permits a diagnostic test for occult blood which produces rapid, easily interpreted and substantially unequivocal test results. This is a consequence of employing for the test an indicator composition which includes a water insoluble fraction of guaiac, an organic hydroperoxide and a buffer system which maintains the pH of the material being tested at a value within the range of about 4.5 to about 6.8 or preferably a test device for the diagnostic test which comprises a matrix, preferably bibulous or cellulosic, treated with the aforementioned indicator composition of the present invention.

BEST MODES FOR CARRYING OUT THE INVENTION

The color indicator system of the present invention provides an indicator composition which is highly sensitive to hemoglobin. This indicator composition includes a water insoluble fraction of guaiac, an organic hydroperoxide, and a buffer system capable of maintaining the pH of the material being tested to within a range of about 4.5 to about 6.8.

Color Indicator

The color indicator of the present invention is a water insoluble fraction of guaiac. As used herein, the terms "water insoluble fraction of guaiac", "water insoluble fraction of gum guaiac", or the like means that material which, when gum guaiac is partitioned between water or an aqueous alkaline solution and an organic solvent such as chloroform or ether, will be found in the organic solvent. The components of this fraction, although not individually characterized, have been collectively shown, with the aid of thin layer chromatography, to contain the compounds most reactive toward peroxides. The water insoluble fraction of guaiac used in the present invention is obtained by dissolving commercially available guaiac resin or gum in chloroform and filtering to remove particulate matter. The chloroform is then washed with a solution of a weakly basic inorganic alkali, such as ammonium hydroxide, sodium bicarbonate, or the like. This is repeated at least once with an additional volume of a more dilute aqueous alkaline solution followed by subsequent washings with water until the water is colorless. The chloroform solution is then washed with four times its volume of petroleum ether in order to precipitate the water insoluble fraction of guaiac which is collected by filtering through a Buchner funnel. The precipitate is then washed with another portion of petroleum ether, filtered and dried in a vacuum oven.

Organic Hydroperoxides

The organic hydroperoxides which are suitable in the indicator compositions of the present invention include, preferably, tertiary hydroperoxide groups, that is, groups in which the hydroperoxide radical is bonded to a carbon atom having three alkyl and/or aryl radicals bound thereto. The tertiary hydroperoxide compounds which are preferred for the present invention may be represented by the general formula

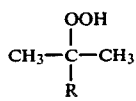

where R may be an alkyl, a cycloalkyl, or an aryl group and is most preferably the latter.

Examples of preferred hydroperoxides of this type include 2,5-dimethylhexane-2,5-dihydroperoxide and paramenthane hydroperoxide. Particularly preferred are isopropylbenzene-type hydroperoxides, such as cumene hydroperoxide and derivatives thereof such as methyl, ethyl and diisopropyl substituted hydroperoxides, particularly the para isomers. The hydroperoxide should be present in the composition in an amount effective to produce a color change when combined with the water insoluble fraction of guaiac and in the presence of a hemoglobin-containing material. This generally is about 10 to about 60 parts, preferably about 11.5 to about 50 parts, by weight, based on one part of the water insoluble fraction of guaiac. When cumene hydroperoxide is employed as the hydroperoxide, it is used preferably in an amount of about 28.5 parts by weight per part of the water insoluble fraction of guaiac.

Buffer Systems

In the test compositions and device of the present invention it is desirable to use buffer systems to maintain the pH of the substance being tested within a suitable acid pH range in order to optimize the test results. A suitable pH range is from about 4.5 to about 6.8, preferably from about 5.2 to about 5.8. When the preferred hydroperoxide, cumene hydroperoxide, is employed, optimum results may be obtained at a pH of 5.4. The latter pH is maintained with a buffer preferably composed of sodium citrate/citric acid. Other pH values within the above-given range may be obtained with buffer pairs of other well known inorganic or organic acids and their salts or acid salts, such as tartrate, phosphate, phthalate, acetate and mixtures of the foregoing.

As indicated above, the buffer system should be present in amounts effective to maintain the pH of the substance being tested within a pH range of about 4.5 to about 6.8. Based on one part of the water insoluble fraction of guaiac, this corresponds, on a dry basis, to about 1 to about 40 parts, preferably about 2 to about 25 parts, by weight of combined acid and salt forms of the buffer. When a citrate buffer is employed, preferably about 2 parts sodium citrate and about 2.8 parts citric acid are used, based on one part, by weight, of the water insoluble fraction of guaiac.

Other Additives

When a cellulosic material, such as paper, is used as the substrate for the test device of the present invention, it is advantageous to use a "binder" or "film former" with the indicator composition. When the preferred hydroperoxide, cumene hydroperoxide, is employed in the indicator composition in combination with a cellulosic material, such as paper, a binder is particularly preferred. The binder appears to improve the distribution and retention of indicator compositions as there is some tendency for the indicator composition to flake off the substrate. However, when a binder is included in the solution of the indicator composition, the components thereof penetrate the surface of the paper and adhere to the paper fibers. Also, when an oily or liquid hydroperoxide, such as cumene hydroperoxide, is employed in the indicator composition, the binder appears to help disperse the hydroperoxide and promote thorough drying throughout the substrate.

Cellulose ethers are suitable for use as binders. The methyl and ethyl cellulose ethers are preferred for this purpose with the former being most preferred.

Based on one part, by weight, of the water insoluble fraction of guaiac, the binder should be present, when used, in amounts of about 0.05 to about 5 parts, preferably about 0.5 to about 3 parts. When methyl cellulose is employed as the binder, about 1.4 parts, by weight, based on one part of the water insoluble fraction of guaiac, may be used.

Additionally, a surfactant may be included in the indicator composition to improve subsequent penetration of the surface of the paper strip by the aqueous portion of the sample being tested. Surfactants or wetting agents suitable for the present invention are substances such as sodium lauryl sulfate, dioctyl sodium sulfosuccinate or one of the long chain monocarboxylates of polyoxyethylene sorbitan, known collectively as the Tweens, such as the monolaurate, the monopalmitate, the monosterate, or the monooleate. Particularly preferred is Tween 80, polyoxyethylene sorbitan monooleate.

When used, the surfactant should be present in amounts of about 0.2 to about 5 parts, preferably about 0.5 to about 3 parts, by weight based on the weight of one part of the water insoluble fraction of guaiac. When Tween 80 is employed as the surfactant, about one part is preferred based, by weight, on one part of the water insoluble fraction of guaiac.

An "extender" for the binder, or a "bulking" agent, may also be included in the composition. Preferred as extenders are sugars, such as lactose or the like, or sugar alcohols, such as mannitol or the like.

When used, the extender should be present in amounts of about 5 parts to about 35 parts, preferably about 8 parts to about 28 parts, by weight, based on the weight of one part of the water insoluble fraction of guaiac. When mannitol is employed as the extender, about 20 parts by weight, based on one part of the water insoluble fraction of guaiac, is preferred.

A solution of either the fundamental indicator composition, which includes the water insoluble fraction of guaiac, an organic hydroperoxide and a buffer system, or a solution suitable for preparation of a test device, which further includes a binder and perhaps a surfactant and an extender, is formed by combining the above described components in the proportions indicated with from about 200 to about 2,000 parts, preferably about 400 to about 1,500 parts, by weight, based on one part of the water insoluble fraction of guaiac of a suitable solvent system. Such a system will preferably include a solvent of a type and in sufficient amount to dissolve the water insoluble fraction of guaiac in the amount employed, as well as the hydroperoxide and buffer system. The solvent preferably includes a water miscible solvent, such as a lower alcohol, preferably ethanol, and some water. Most preferred is a solution approximately 1:1 (v/v) ethanol:water.

A preferred indicator composition according to the present invention is as follows:

| Component | Parts By Weight |
| --- | --- |
| Water Insoluble Fraction of Guaiac | 1.0 |
| Cumene Hydroperoxide | 28.6 |
| Sodium Citrate | 2.0 |
| Citric Acid | 2.8 |
| 1:1 (v/v) Ethanol:Water | 800 |

A preferred composition for the test device of the present invention is as follows:

| Component | Parts By Weight |
| --- | --- |
| Water Insoluble Fraction of Guaiac | 1.0 |
| Cumene Hydroperoxide | 28.6 |
| Sodium Citrate | 2.0 |
| Citric Acid | 2.8 |
| Methyl Cellulose | 1.4 |
| Mannitol | 20.0 |
| Tween 80 | 1.0 |
| Filter Paper | 196 |

Preparation of Indicator Composition and Test Device

To form the indicator compositions of the present invention which may be used to detect hemoglobin in occult blood from whatever source, the following procedure may be used. The proportions of reagents employed in the procedure are as indicated above.

A solution of the fundamental indicator composition of the present invention may be prepared by combining a suitable amount of the water insoluble fraction of guaiac described above with 95 percent ethanol with sufficient stirring to effect solution. Thereafter, the organic hydroperoxide is combined with the ethanolic solution with suitable agitation to bring the hydroperoxide into solution When the indicator composition is to be used to prepare a test device according to the present invention, such as by impregnating a cellulosic matrix, a surfactant, such as Tween 80, may be added along with the water insoluble fraction of guaiac to the ethanol.

A suitable buffer solution is combined with the water insoluble fraction of guaiac and hydroperoxide (and surfactant if the indicator solution is to be used with a test device using a cellulosic matrix). Commercially available buffer solutions may be employed in amounts suitable to bring a sample being tested within the pH range indicated above or to produce the above-indicated dry weights of buffering systems. Alternatively, a buffering system solution may be freshly prepared. For example, the preferred citrate buffer system may be prepared by combining about 2 parts of sodium citrate and about 2.8 parts of citric acid with, preferably, about 80 parts by weight of distilled water for each one part of the water insoluble fraction of guaiac employed.

When the indicator composition is used as a solution to impregnate a matrix preferably a cellulosic one, such as paper, the solution preferably contains a binder and an extender. These last mentioned materials are preferably introduced as a separate solution to the buffer solution before the latter is combined with the solution of the water insoluble fraction of guaiac, hydroperoxide and surfactant. Thus, a binder/extender solution may be prepared by combining the methyl cellulose with sufficient distilled water, preferably about 175 parts by weight based on the weight of one part of the water insoluble fraction of guaiac. This mixture is heated to a temperature above 50 degrees C., preferably about 65 degrees C., and thereafter cooled to a temperature below about 8 degrees C., preferably about 5 degrees C., for a period of about eight hours or more, conveniently overnight. Thereafter, an extender, such as mannitol, is combined with the binder solution with sufficient agitation to dissolve the extender. The resulting solution is then combined with the buffer solution and the buffer/binder/extender solution is combined with the solution of water insoluble guaiac/hydroperoxide/surfactant.

The above-described buffered indicator composition containing the water insoluble fraction of guaiac, hydroperoxide and buffer may be used to test for occult blood simply by mixing with a specific amount of water in a suitable container and introducing a sample suspected of containing occult blood to the container. It is preferred, however, to impregnate a matrix, preferably a bibulous one, with the buffered indicator solution, dry the impregated matrix and use it as a test device, as needed. Cellulosic materials, such as paper or wood, in strip or stick form, are preferred. When paper, the most preferred matrix, is employed, it is impregnated by immersing the paper in the buffered solution of the indicator and thereafter dried. Filter paper is particularly preferred because of its absorbency and preferred filter papers provide good wet strength and penetrability. Filter papers having a thickness from about 0.008 to about 0.013 inches are preferred, although other thickness papers, preferably thicker ones, may also be employed. The preferred thicknesses allow an adequate concentration of indicator composition. The paper preferably is present in an amount of about 50 to about 300 parts be weight, based on one part of the water insoluble fraction of guaiac.

Both the indicator composition and the indicator test device of the present invention are simple to use. As indicated above, the buffered indicator solution may be used directly after dilution with a suitable amount of water. When an impregnated bibulous cellulosic strip, such as a paper strip, is employed, a sample of the material being tested for occult blood may be applied directly to the paper strip and that side of the strip, or preferably the reverse side of the strip may be examined for development of blue color within seconds of applying the sample. The sample may be any liquid bodily fluid or excreta, applied directly, or the latter may be extracted or triturated and the extract applied to the test strip. In most instances, however, this latter procedure is unnecessary.

The test devices according to the present invention, particularaly those employing filter paper as the cellulosic substrate, demonstrate sensitivity to whole blood to as little as 0.006 mg/ml whole blood. These devices tend to demonstrate slightly greater sensitivity to occult blood in feces samples than in urine samples.

The present invention will be more clearly understood by reference to the following illustrative examples. The scope of the present invention, however, should not be construed as being limited in any way to the specific details of these examples.

Example 1, Preparation of A Water Insoluble Fraction of Guaiac Gum

In about one liter of chloroform were dissolved 40 grams of gum guaiac. After stirring for 25 minutes, the chloroform solution was gravity filtered to remove insoluble material. The filtered chloroform solution was then placed in a separatory funnel and washed successively with 500 ml of 10 percent, by weight, NH₄OH solution, 500 ml of 5 percent, by weight, NH₄OH solution, and 500 ml portions of distilled water. Sufficient washings with distilled water were performed until the water phase was colorless. The volume of the chloroform solution was then measured and four times its volume of petroleum ether (boiling point 65 degrees C) was added and agitated to precipitate the water insoluble fraction of guaiac. The precipitated fraction of water insoluble guaiac was collected on a Buchner funnel and washed with 200 milliliters of the pertroleum ether. The precipitate was then dried in a vacuum oven at about 45 degrees C for 3 hours. This procedure yielded about 14.2 grams of water insoluble guaiac.

Example 2, Preparation of Methyl Cellulose/Mannitol Solution

To 220 milliliters of distilled water was added, with stirring, 1.725 grams of methylcellulose. The mixture was heated to 65 degrees C and stored overnight at 5 degrees C. The methylcellulose solution was thereafter combined with 25 grams of mannitol with sufficient agitation to dissolve the latter.

Example 3, Preparation of Citrate Buffer Solution

To 100 milliliters of distilled water was added, with stirring, 2.5 grams of sodium citrate and 3.5 grams of citric acid. The pH of the resulting buffer solution was 5.4.

Example 4, Preparation of Guaiac Indicator/Hydroperoxide Solution

Approximately 300 milliliters of 95 percent ethanol was combined with stirring, with 1.25 grams of the insoluble fraction of guaiac and upon complete solution there was further added 37.5 ml (35.7 grams) of cumene hydroperoxide with sufficient stirring to effect solution.

Example 5, Indicator/Hydroperoxide/ Surfactant Solution

An indicator/hydroperoxide solution was prepared using the same substances, quantities and procedure as in Example 4. In addition, however, to the insoluble fraction of guaiac there was added to the ethanol 1.25 grams of Tween 80 with the insoluble fraction of guaiac.

Example 6, Preparation of Cellulosic Impregnated Test Devices

The solution resulting from Example 3 was combined with the solution resulting from Example 2. After thorough mixing, the solution resulting from Example 5 was slowly added to the combined solution resulting from Examples 2 and 3. The latter solution (combined solution from Examples 2, 3 and 5), or paper impregnating solution, was placed in a shallow pan and a 6 inch x 18 inch sheet of filter paper was placed in the treating solution for about 10 seconds. The sheet was hung up to dry in a drying oven at 135 degrees F for a period of less than five minutes. The paper impregnating solution was sufficient to prepare twenty-five 18 inch by 6 inch sheets.

Example 7, Test for Presence of Occult Blood in Feces

One of the sheets prepared in Example 6 was cut into 2 inch by 2 inch quares. To one surface of one of the squares was dabbed a sample of feces known to contain occult blood. The moisture in the sample was sufficient to moisten the area to which the same was applied. After five seconds, a blue spot began to develop on the surface of the paper opposite that on which the feces had been deposited.

It should be clearly understood by those skilled in the art that certain changes may be made in the foregoing compositions and methods without departing from the spirit and scope of the invention described herein. It is also intended that all matter contained in the foregoing examples shall be interpreted as being illustrative and not in any way limiting from the scope of the invention.

I claim:

1. A substantially dry test device for detecting occult blood comprising:
    a test matrix of bibulous material impregnated with an indicator composition including:
    a color indicator consisting essentially of an alkaline water insoluble fraction of guaiac which is soluble in an organic solvent;
    an organic hydroperoxide containing a tertiary hydroperoxide group; and
    a buffer capable of maintaining the pH of a material being tested at a value within the range of about 4.5 to about 6.8, said organic hydroperoxide, said alkaline water insoluble fraction of guaiac and said buffer being present in amounts suitable to effect a color change in said test device in the presence of a hemoglobin containing material.

2. The test device according to claim 1 wherein said organic hydroperoxide is cumene hydroperoxide.

3. The test device according to claim 1 wherein said organic hydroperoxide is present in an amount of about 10 to about 60 parts and said buffer is present in an amount of about 1 to about 40 parts, all parts being by weight based on one part of said alkaline water insoluble fraction of guaiac.

4. The test device according to claim 1 wherein said bibulous material is paper and is present in an amount of about 50 to about 300 parts by weight, based on one part of the alkaline water insoluble fraction of guaiac.

5. The test device according to claim 1 further includng a binder effective to cause the indicator composition to adhere to said matrix.

6. The test device according to claim 1 further including an extender.

7. The test device according to claim 1 wherein said bibulous material is paper present in an amount of about 50 to about 300 parts by weight, based on one part of said alkaline water insoluble fraction of guaiac, said organic hydroperoxide is cumene hydroperoxide present in an amount of about 11.5 to about 50 parts by weight based on the weight of one part of said alkaline water insoluble fraction of guaiac, said buffer is a citric acid/citrate salt buffer system present in an amount of about 2 to about 25 parts by weight, based on the weight of one part of said alkaline water insoluble fraction of guaiac, and further including methyl cellulose, mannitol and polyoxyethylene sorbitan monoleate.

8. A test composition for detection of occult blood comprising:
    a color indicator consisting essentially of an alkaline water insoluble fraction of guaiac which is soluble in organic solvent;
    an organic hydroperoxide containing a tertiary hydroperoxide group; and a buffer capable of maintaining the pH of a material being tested within the range of about 4.5 to about 6.8, said alkaline water insoluble fraction of guaiac, said hydroperoxide and said buffer being present in amounts effective to produce a color change in the presence of a hemoglobin containing material.

9. The test composition according to claim 8 wherein said hydroperoxide is cumene hydroperoxide.

10. The test composition according to claim 8 wherein said organic hydroperoxide is present in an amount of about 10 to about 60 parts and said buffer in an amount of about 1 to about 40 parts, all parts being by weight based on one part of said alkaline water insoluble fraction of guaiac.

11. The test composition according to claim 8 including a water miscible solvent system.

12. The test composition according to claim 8 further including a binder effective to cause the test composition to adhere to a matrix.

13. The test composition according to claim 8 further including an extender.

14. The test composition according to claim 8 wherein said organic hydroperoxide is cumene hydroperoxide present in an amount of about 11.5 to about 50 parts by weight, based on the weight of one part of said alkaline water insoluble fraction of guaiac, said buffer is a citric acid/citrate salt buffer system present in an amount of about 2 to about 25 parts by weight, based on the weight of one part of said alkaline water insoluble fraction of guaiac, and further including methyl cellulose, mannitol, and polyoxyethylene sorbitan monoleate and a mixture of ethanol and water.

* * * * *